United States Patent
Liu et al.

(10) Patent No.: US 10,471,274 B2
(45) Date of Patent: Nov. 12, 2019

(54) PULSE WIDTH MODULATION CONTROL FOR BATTERY-POWERED LASER DEVICE

(71) Applicant: TRIA Beauty, Inc., Dublin, CA (US)

(72) Inventors: Harvey I-Heng Liu, Fremont, CA (US); John P. Beale, Mountain View, CA (US)

(73) Assignee: CHANNEL INVESTMENTS, LLC, Tampa, FL (US)

( * ) Notice: Subject to any disclaimer, the term of this patent is extended or adjusted under 35 U.S.C. 154(b) by 0 days.

(21) Appl. No.: 14/167,113

(22) Filed: Jan. 29, 2014

(65) Prior Publication Data

US 2014/0214136 A1 Jul. 31, 2014

Related U.S. Application Data

(60) Provisional application No. 61/758,609, filed on Jan. 30, 2013.

(51) Int. Cl.
| | |
|---|---|
| *A61N 5/06* | (2006.01) |
| *A61B 18/20* | (2006.01) |
| *A61B 17/00* | (2006.01) |
| *A61B 18/00* | (2006.01) |
| *A61B 18/22* | (2006.01) |
| *A61B 90/00* | (2016.01) |

(52) U.S. Cl.
CPC .......... *A61N 5/0616* (2013.01); *A61B 18/203* (2013.01); *A61B 2017/00057* (2013.01); *A61B 2017/00075* (2013.01); *A61B 2017/00141* (2013.01); *A61B 2017/00159* (2013.01); *A61B 2017/00734* (2013.01); *A61B 2017/00761* (2013.01); *A61B 2017/00765* (2013.01);

(Continued)

(58) Field of Classification Search
CPC .... A61B 18/20–18/28; A61N 5/06–2005/073; A61F 7/00–2007/126
See application file for complete search history.

(56) References Cited

U.S. PATENT DOCUMENTS 6,157,661 A    12/2000  Walker et al. ............. 372/38.02
6,304,475 B1 *  10/2001  Iwata ................... H01S 3/0975
                                                    363/132

(Continued)

OTHER PUBLICATIONS

International Search Report and Written Opinion, Application No. PCT/US2014/013577, 12 pages, dated Apr. 30, 2014.

*Primary Examiner* — Gary Jackson
*Assistant Examiner* — Jonathan Kuo
(74) *Attorney, Agent, or Firm* — Slayden Grubert Beard PLLC

(57) ABSTRACT

A battery-powered laser-based dermatological treatment device may include a laser unit comprising at least one laser diode, a battery unit, at least one sensor configured to generate sensor signals, and a laser drive control system including a laser drive circuit comprising the laser unit, the battery unit, a first switch (e.g., a first FET), and a second switch (e.g., a second FET), wherein the laser unit is arranged in series between the first switch and the second switch, and control electronics configured to control the first switch based at least on sensor signals from the at least one sensor, and control the second switch using pulse width modulation (PWM), thereby delivering current from the battery unit to the laser unit with a PWM current waveform. The laser drive circuit may also include a snubber circuit configured to prevent voltage spikes upon the second switch being turned off.

16 Claims, 3 Drawing Sheets

(52) U.S. Cl.
CPC ............... *A61B 2017/00769* (2013.01); *A61B 2018/0047* (2013.01); *A61B 2018/00452* (2013.01); *A61B 2018/00476* (2013.01); *A61B 2018/00642* (2013.01); *A61B 2018/00773* (2013.01); *A61B 2018/00791* (2013.01); *A61B 2018/2261* (2013.01); *A61B 2090/065* (2016.02)

(56) References Cited

U.S. PATENT DOCUMENTS

| | | | | |
|---|---|---|---|---|
| 6,595,985 | B1 * | 7/2003 | Tobinick | A61B 18/203 606/13 |
| 7,208,916 | B1 * | 4/2007 | Boatwright | H01M 10/486 320/150 |
| 7,452,356 | B2 * | 11/2008 | Grove | A61B 18/203 606/10 |
| 9,078,680 | B2 * | 7/2015 | Lemberg | A61B 18/203 |
| 2003/0018324 | A1 * | 1/2003 | Davenport | A61B 18/22 606/3 |
| 2005/0085875 | A1 * | 4/2005 | Van Zuylen | A61N 5/0616 607/88 |
| 2007/0093798 | A1 * | 4/2007 | DeBenedictis | A61B 18/203 606/12 |
| 2009/0222068 | A1 * | 9/2009 | Oberreiter | A61B 18/203 607/88 |
| 2010/0196343 | A1 * | 8/2010 | O'Neil | A61B 18/203 424/94.4 |
| 2012/0041523 | A1 * | 2/2012 | Solomon | A61N 5/0616 607/90 |
| 2012/0253334 | A1 | 10/2012 | Liu et al. | 606/9 |

* cited by examiner

PULSE WIDTH MODULATION CONTROL FOR BATTERY-POWERED LASER DEVICE

CROSS-REFERENCE TO RELATED APPLICATIONS

This application claims the benefit of U.S. Provisional Application No. 61/758,609 filed on Jan. 30, 2013, which disclosure is herein incorporated by reference in its entirety.

TECHNICAL FIELD

The present disclosure is related to a pulse width modulation (PWM) control for a battery-powered device, e.g., a handheld laser-based dermatological treatment device.

BACKGROUND

Laser-based treatment of tissue is used for a variety of applications, such as hair removal, skin rejuvenation, wrinkle treatment, acne treatment, treatment of vascular lesions (e.g., spider veins, diffuse redness, etc.), treatment of cellulite, treatment of pigmented legions (e.g., age spots, sun spots, moles, etc.), tattoo removal, and various other treatments. Such treatments generally include delivering laser radiation to an area of tissue on a person's body, e.g., the skin or internal tissue, to treat the tissue in a photochemical, photobiological, thermal, or other manner, which can be ablative or non-ablative, among other properties, depending on the particular application.

Laser-based treatment devices may include any suitable type of laser, e.g., laser diode, fiber laser, VCSEL (Vertical Cavity Surface Emitting Laser), LED, etc. A device may include a single laser or multiple lasers, e.g., a laser diode bar including multiple distinct emitters arranged in a row, or multiple fiber lasers arranged in a row or array.

Diode lasers are particularly suitable for certain treatments and devices for providing such treatments. For example, diode lasers are compact, as they are typically built on one chip that contains all necessary components. Further, diode lasers typically provide an efficiency of up to 50%, which enables them to be driven by low electrical power compared to certain other lasers. Further, diode lasers allow direct excitation with small electric currents, such that conventional transistor based circuits can be used to power the laser.

Other characteristics of diode lasers include high temperature sensitivity/tunability, and a highly divergent beam compared to certain other lasers. Diode lasers typically emit a beam having an axis-asymmetric profile in a plane transverse to the optical axis of the laser. In particular, the emitted beam diverges significantly faster in a first axis (referred to as the "fast axis") than in an orthogonal second axis (referred to as the "slow axis"). In contrast, other types of lasers, e.g., fiber lasers, typically emit a beam having an axis-symmetric profile in the transverse plane.

Laser-based treatment devices include larger-scale devices typically operated by a physician or other professional in a clinic or other office, as well as hand-held devices for home-use, allowing users to provide treatment to themselves. Some hand-held laser-based treatment devices are battery powered, e.g., using a Li ion battery cell (or multiple cells). Such battery-powered devices may be recharged between use, e.g., by plugging into an A/C wall outlet, either directly or by docking in a docking unit plugged into the wall.

Laser-based treatment devices are typically high current devices, in order to drive the laser(s) to generate the desired laser radiation. Battery-powered laser-based treatment devices include a control system to apply a relatively high current, e.g., 30-120 A from the battery to the laser(s) to generate the desired laser radiation for delivery to the skin. Battery-powered laser-based treatment devices often use a linear constant-current control system, with analog control.

FIG. 1 shows an example linear control system for providing constant-current from a battery to a laser diode LD. As shown, a continually varying voltage is generated by an analog circuit, which may include one or more op-amps, resistors, and/or other electronic components, which applies a gate voltage to a control FET (field effect transistor), which voltage is between the voltage that turns the FET fully OFF, Vg(off), and the voltage that turns the FET fully ON, Vg(on). In this way, the FET acts as a voltage-controlled resistor that dissipates significant power as it controls the current flowing through the laser diode LD and the rest of the circuit. The analog control circuit typically requires a number of parts, which may be expensive and have accuracy requirements and calibration requirements.

The high power dissipation of the control FET generates heat on the circuit board, which may negatively affect other parts of the circuit, and may cause reliability issues. Such unwanted heat may be relatively difficult and expensive to remove from the device. In the example shown in FIG. 1, an analog current-sense amp measures the current, and this analog voltage is used by the control system, and also read into a CPU. This analog current sensing is needed for the analog linear control system to provide a closed-loop feedback circuit that operates on a short timescale, e.g., as compared with the duration of a laser pulse.

SUMMARY

Embodiments of the present disclosure provide a battery-powered laser device using digital pulse width modulation (PWM) control, rather than analog linear control used in certain conventional devices. Using PWM may enable the number of components in the control system to be reduced, thereby lowering the overall cost of the device. It may also reduce the heat generated on the circuit board (PCB), where it is unwanted and expensive to remove, and instead generate additional heating (specifically, $I^2R$ heating) at the battery, where an increased temperature increases the total available energy from the battery.

Thus, as opposed to existing designs that use a linear control system for the laser, embodiments disclosed herein provide a unique solution for driving a laser using PWM control, which increases or maximizes the amount of available energy delivered from the battery to the laser, while reducing minimizing the amount of heat dissipated on the circuit board, and with a lower BOM (bill of materials) cost than certain existing linear control systems.

One embodiment of the present disclosure provides a battery-powered laser-based dermatological treatment device may include a laser unit comprising at least one laser diode, a battery unit, at least one sensor configured to generate sensor signals, and a laser drive control system including a laser drive circuit comprising the laser unit, the battery unit, a first switch (e.g., a first FET), and a second switch (e.g., a second FET), wherein the laser unit is arranged in series between the first switch and the second switch, and control electronics configured to control the first switch based at least on sensor signals from the at least one sensor, and control the second switch using pulse width modulation (PWM), thereby delivering current from the battery unit to the laser unit with a PWM current waveform. The laser drive circuit may also include a snubber circuit configured to prevent voltage spikes upon the second switch being turned off.

Another embodiment of the present disclosure provides a control system for a dermatological treatment device including a laser unit comprising at least one laser diode, a battery unit, and at least one sensor configured to generate sensor signals. The control system comprises a laser drive circuit comprising the laser unit, the battery unit, a first switch, and a second switch, wherein the laser unit is arranged in series between the first switch and the second switch; and control electronics configured to control the first switch based at least on sensor signals from the at least one sensor, and control the second switch using pulse width modulation (PWM), thereby delivering current from the battery unit to the laser unit with a PWM current waveform.

BRIEF DESCRIPTION OF THE DRAWINGS

Some embodiments of the disclosure may be understood by referring, in part, to the following description and the accompanying drawings wherein.

DETAILED DESCRIPTION OF THE DRAWINGS

Some embodiments of the disclosure may be understood by referring, in part, to the following description and the accompanying drawings, in which like reference numbers refer to the same or like parts.

Figure 1:
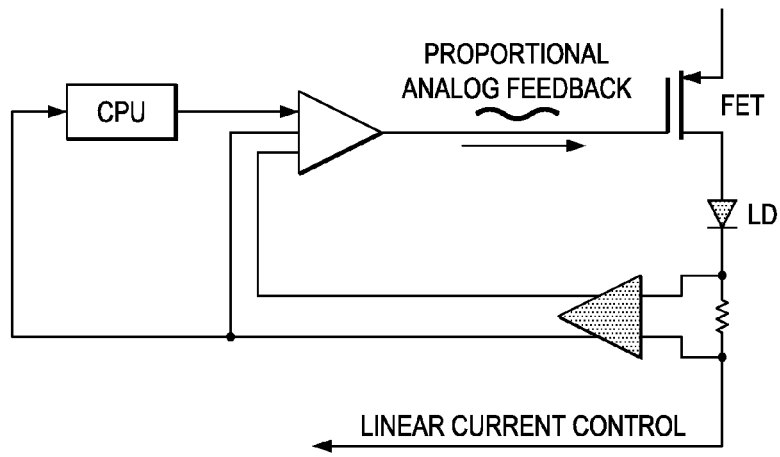
FIG. 1 illustrates an example of a conventional linear control system for a battery-operated laser device.
Figure 2:
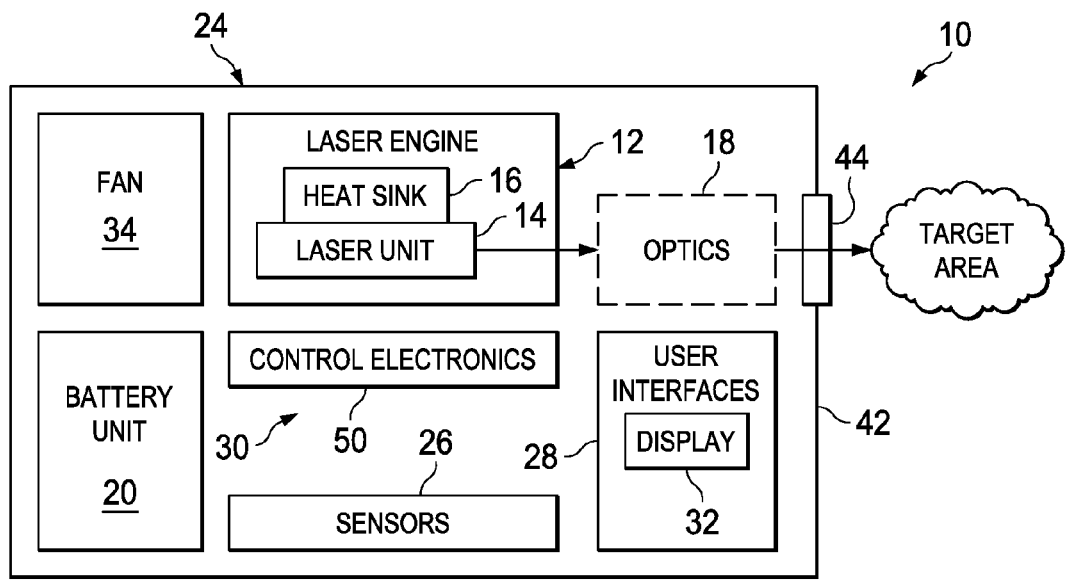
FIG. 2 illustrates components of an example battery-powered laser device including a PWM control system, for providing a dermatological treatment, according to certain embodiments of the present invention.

FIG. 2 illustrates components of an example treatment device 10, according to certain embodiments. Treatment device 10 may include a laser engine 12 including a laser unit 14 configured to generate laser radiation, (optional) optics 18 for delivering the laser radiation to a target area 40 (e.g., an area of tissue), a battery unit 20 for supplying power to the laser engine 12, one or more fans 34, one or more sensors 26 for detecting various parameters, one or more user interfaces 28, and a laser control system 30 for controlling the laser unit 14, e.g., by controlling laser unit 14 based on input from sensors 26 and/or user interfaces 28, and by supplying power from the battery unit 20 to the laser unit 14 via pulse width modulated (PWM) control.

The components of device 10 may be provided in a structure or housing 24, or alternatively may be provided in separate structures or housings and connected in any suitable manner, e.g., via fiber optic or other cabling. Housing 24 may define an application end (or "treatment tip") 42 configured to be placed in contact with the target surface (e.g., skin) during treatment of the target area 40. Application end 42 may include or house various user interfaces, including the treatment delivery interface for delivering output beams to the user, as well as one or more sensors 26 for detecting various characteristics of the target surface and/or treatment delivered by device 10. In some embodiments, application end 42 may include an aperture or window 44 through which the laser beam is delivered to the target surface, or alternatively, an optical element 18 (e.g., a lens or diffuser) may be located at application end 42 and configured for direct contact or very close proximity with the skin during treatment.

Device 10 may include any other components suitable for providing any of the functionality discussed herein or other related functionality known to one of ordinary skill in the art.

Laser engine 12 may include laser unit 14 coupled to a heat sink 16. Laser unit 14 may include one or more lasers configured to generate one or more laser beams for delivery to the skin. Laser unit 14 may include any one or more types and numbers of laser devices. For example, laser unit 14 may include one or more single-emitter or dual-emitter laser diodes, or one or more multiple-emitter laser diode bars. Laser unit 14 may be configured for and/or operated at any suitable wavelength to provide the desired treatment. For example, laser unit 14 may be configured for and/or operated at a wavelength of between 650 and 1100 nm (e.g., 810 nm±30 nm) for providing hair removal treatment. As another example, laser unit 14 may be configured for and/or operated at a wavelength that is absorbed by water in the skin, e.g., between 1400 nm and 2000 nm, e.g., for certain photothermolysis treatments. In some embodiments, laser unit 14 may be configured for and/or operated at a wavelength of between 1400 nm and 1550 nm, e.g., for acne treatment or certain fractional non-ablative skin treatments. In other embodiments, laser unit 14 may be configured for and/or operated at a wavelength of between 1700 nm and 1800 nm, e.g., for sebaceous gland related treatment like acne. In still other embodiments, laser unit 14 may be configured for and/or operated at a wavelength of between 1900 nm and 1950 nm, e.g., for pigmented lesion treatment like solar lentigo.

Further, laser unit 14 may be configured or operated to deliver continuous wave (CW) radiation, pulsed radiation, or in any other manner. In some embodiments, laser control system 30 controls laser unit 14 to provide CW radiation, e.g., for using device 10 in a gliding mode for hair removal, bulk heating skin tightening, or acne treatment. In other embodiments, laser control system 30 controls laser unit 14 to provide pulsed radiation (distinct from the PWM pulsing, as discussed below). As discussed herein, in pulsed radiation, laser unit 14 delivers a series of discrete "treatment pulses." For example, laser unit 14 may provide user-triggered pulsed radiation, e.g., for using device 10 in a stamping mode for hair removal. Pulses may be manually triggered in any suitable manner, e.g., by pressing a button to initiate each pulse. In still other embodiments, laser control system 30 controls laser unit 14 to provide automatically pulsed radiation, e.g., for using device 10 in a gliding mode for hair removal or selective photothermalysis. For example, in some embodiments, device 10 may be configured to sequentially deliver a series of laser beams to the target area 40 to generate overlapping treatment spots, edge-to-edge adjacent treatment spots, or spaced-apart treatment spots (fractional treatment) on the skin, e.g., for a hair removal treatment, skin rejuvenation, wrinkle treatment, treatment of pigmented legions, etc. In automatically pulsed radiation, treatment pulses may be initiated or controlled automatically, e.g., according to a predefined pulse frequency or automatically upon some triggering event, such as automatic pulse triggering upon a predetermined displacement of device 10 moving across the skin, or automatic pulse triggering upon re-triggering of a capacitive skin contact sensor by lifting and placing the device tip on a different spot, for example. Such embodiments may utilize any suitable pulse parameters, e.g., pulse rate or frequency, pulse-on duration (pulse width), pulse-off duration, duty cycle, pulse profile, etc.

Laser unit 14 may be pulsed with any suitable pulse duration and radiation profile. For example, certain embodiments configured for hair removal may pulse laser unit 14 with a pulse duration of 50-700 ms. As another example, certain embodiments configured for providing fractional treatment (e.g., for skin rejuvenation or wrinkle treatment) may pulse laser unit 14 with a pulse duration of 1-20 ms.

As discussed above, laser control system 30 may power laser unit 14 (from battery unit 20) using pulse width modulated (PWM) control. Thus, it is important to understand the distinction and interaction between (a) "continuous wave" (CW) radiation and "pulsed radiation" discussed above, and (b) the pulsed current profile provided by PWM control of laser unit 14. In a typical application, the PWM control provides a pulsed current wavelength with very high frequency, e.g., 15-40 kHz, with a very short pulse width (pulse-on duration), e.g., 10-50 $\mu$sec. These pulses generated by PWM control are referred to herein as "PWM pulses."

PWM pulses typically have a much shorter pulse width, and much higher frequency, than "treatment pulses" provided in pulsed radiation. For example, in certain embodiments configured to provide a hair removal treatment using automatically pulsed radiation, the treatment pulse frequency may be between 0.25 and 2 Hz with a pulse width (pulse-on duration) of between 50 and 700 msec. In particular hair removal embodiments, the treatment pulse frequency may be between 0.25 and 1 Hz with a pulse width (pulse-on duration) of between 100 and 500 msec. As another example, in certain embodiments configured to provide a fractional treatment using automatically pulsed radiation, the treatment pulse frequency may be between 2 and 30 Hz with a pulse width (pulse-on duration) of between 0.5 and 10 msec. In particular hair removal embodiments, the treatment pulse frequency may be between 10 and 20 Hz with a pulse width (pulse-on duration) of between 2 and 5 msec.

Due to the very high frequency of the PWM pulsing and energy absorption characteristics of the skin, the pulsed PWM waveform is effectively buffered by the skin, such that each treatment pulse (which includes many PWM pulses) is seen by the skin as a continuous pulse of radiation.

Thus, for CW radiation, it should be understood that CW radiation with PWM control is still considered herein as "continuous wave" because the high-frequency PWM pulsing is buffered by the skin, such that the skin experiences the radiation as a continuous flux.

Heat sink 16 for managing heat produced by the laser unit 14 and/or other components of device 10, e.g., any heat-generating electronics of laser control system 30. Heat sink 16 may be a separate structure from laser package 14, or may be integrated into laser package 14 (e.g., a carrier or submount of the laser package may act as the heat sink). In some embodiments, heat sink 16 may be cooled by one or more fans 34, e.g., to increase convective heat transfer away from device 10. Laser engine 12 may also include electrical connections and/or electronics for providing power to, and controlling the operation of, laser unit 14. For example, laser engine 12 may include certain electronics for controlling laser unit 14, such that laser engine 12 and laser control system 30 are at least partially integrated.

Some embodiments of device 10 include one or more optics 18 downstream of laser unit 14 for directing or treating the laser radiation emitted by laser unit 14 before reaching the target surface. Optics 18 may include any number and types of optical elements, e.g., lenses, mirrors, diffusers, and other reflective and/or fully or partially transmissive elements or surfaces, for delivering the radiation generated by laser engine 12 (e.g., in the form of one or more beams) to the target area 40 and, if desired, for treating the radiation, such as adjusting the treatment zone size, intensity, treatment zone location, angular distribution, coherence, etc. In some embodiments, optics 18 may include an automated scanning system for scanning a pattern of treatment zones in the target area 40, e.g., as disclosed in application U.S. Ser. No. 13/443,717 filed Apr. 10, 2012, the contents of which application are hereby incorporated in their entirety.

As used herein, an "optic" or "optical element" may mean any element that deflects a light beam, influences the angular distribution profile (e.g., angle of convergence, divergence, or collimation) of a laser beam in at least one axis, influences the focus of the beam in at least one axis, or otherwise affects a property of the radiation. Thus, optics include mirrors and other reflective surfaces, lenses, prisms, light guides, reflective mixing chambers, gratings, filters, diffusers, etc. For the purposes of this disclosure, optics do not generally include planar or substantially planar transmissive elements such as transmissive windows or films, such as those that serve as transmissive aperture that protect internal components.

One example embodiment configured for hair removal includes a cylindrical solid light guide, or mixer, downstream of the laser, which light guide may be surrounded along its length by a reflective cylindrical surface, e.g., a reflective outer coating may be applied to the exterior of the light guide, or the light guide may be received in a cylindrical opening formed in an outer member (e.g., heat sink) that defines a reflective surface around the light guide. The light guide may be arranged such that laser radiation from laser unit 14 is radiated into an input end of the light guide, and becomes distributed or "mixed" within the light guide such that the radiation is substantially uniformly distributed across the opposite, output end of the light guide. In some embodiments, radiation may be emitted from the output end of the light guide and to the target surface (skin). In other embodiments, one or more additional optics, e.g., a diffuser, lens, or other optic(s), may be arranged downstream of the output end of the light guide. For example, a diffuser may be arranged over the output end of the light guide, and configured to further diffuse the radiation from the light guide, e.g., to provide a further degree of eye safety for radiation emitted from device 10, e.g., a diffuser as disclosed in U.S. Pat. No. 7,452,356, which is hereby incorporated by reference.

In other embodiments, a hollow mixer (e.g., a cylindrical tube) with reflective inner walls may be used instead of a solid light guide, which may similarly act to distribute or "mix" the radiation emitted by laser unit 14. In some embodiments, the output end of the hollow mixer may be open, or covered by a transmissive window or film. In other embodiments, one or more optics, e.g., a diffuser, lens, or other optic(s), may be arranged at or downstream of the output end of the hollow mixer. For example, a diffuser may be arranged over the output end of the hollow mixer, and configured to further diffuse the radiation from the light guide, e.g., similar to the arrangement disclosed in U.S. Pat. No. 7,452,356, which is hereby incorporated by reference.

Other embodiments of device 10 do not include any optics 18 downstream of laser unit 14. Such embodiments have an open treatment aperture, or may include a window, e.g., to protect the laser emitter(s) and/or other internal components of the device. A window may be formed from any suitable material, e.g., sapphire, quartz, diamond, or other material transparent at the wavelength of the laser unit 14 and preferably also having a good thermal coefficient.

Laser control system 30 may be configured to control laser unit 14 based on input received from various inputs, e.g., sensors 26, user interfaces 28, and/or other data inputs. Laser control system 30 may include control electronics 50 configured to control the operation of various electronic devices, e.g., one or more switches (e.g., FETs). Control electronics 50 may include one or more processing devices, memory devices for storing logic instructions or algorithms or other data, and other suitable components. Memory devices may include any one or more device for storing electronic data (including logic instructions or algorithms), such as any type of RAM, ROM, Flash memory, or any other suitable volatile and/or non-volatile memory devices. Logic instructions or algorithms may be implemented as software, firmware, or any combination thereof. Processors may include any one or more devices, e.g., one or more microprocessors and/or microcontrollers, for executing logic instructions or algorithms (e.g., embodied as software or firmware) to control the delivery of current from battery unit 20 to laser unit 14 to generate laser radiation as desired.

Laser control system 30 may be configured to control laser unit 14 according to one or more operational parameters of device 10. For example, laser control system 30 may control laser unit 14 according to a selected treatment level (e.g., low power level, medium power level, or high power level) or treatment mode (e.g., gliding mode vs. stamping mode; or manually pulsed mode vs. automatically pulsed mode; or rapid-pulse mode vs. slow-pulse mode; or initial treatment mode vs. subsequent treatment mode; etc.). Laser control system 30 may one or more operational parameters of control laser unit 14, or individual lasers of laser unit 14, such as on/off status, pulse-on time, pulse-off time, pulse duty cycle, pulse frequency, temporal pulse pattern, etc., parameters of the radiation emitted by laser unit 14 (e.g., radiation wavelength, intensity, power, fluence, etc.), and/or any other aspects of laser unit 14.

As discussed above, laser control system 30 may control laser unit 14 using PWM control. Laser control system 30 is discussed in more detail below with reference to FIGS. 3-5.

Sensors 26 may include any one or more sensors or sensor systems for sensing or detecting data regarding device 10, the user, the operating environment, or any other relevant parameters. For example, sensors 26 may include one or more of the following types of sensors: (a) one or more displacement sensor for determining the displacement of device 10 relative to the skin as device 10 is moved (e.g., glided) across the skin, (b) one or more glide speed sensor for determining the speed, rate, or velocity of device 10 moving (e.g., gliding) across the skin, (c) one or more skin-contact sensor for detecting proper contact between device 10 and the skin, (d) one or more pressure sensor for detecting the pressure of device 10 pressed against the skin, (e) one or more temperature sensor for detecting the temperature of the skin, a region of the skin, and/or components of device 10, (f) one or more radiation sensor for detecting one or more parameters of radiation (e.g., intensity, fluence, wavelength, etc.) delivered to the skin, (g) one or more color/pigment sensor for detecting the color or level of pigmentation in the skin, (h) one or more treatment endpoint sensor, e.g., a color/pigment sensor, for detecting an influence of the radiation on the skin (e.g., erythema, temperature, perifollicular edema, etc.) during or after a treatment, (i) one or more eye safety sensor for preventing unwanted eye exposure to light from laser unit 14, (j) one or more dwell sensor for detecting if the device is stationary or essentially stationary with respect to the skin, (k) one or more roller-type sensors for detecting the displacement and/or glide speed of device 10, (l) one or more imaging sensors for determining pre-treatment skin condition such as texture or hair count for setting subsequent treatment parameters, and/or any (m) other suitable types of sensors.

User interfaces 28 may include any systems for facilitating user interaction with device 10. For example, user interfaces 28 may include buttons, switches, knobs, sliders, touch screens, keypads, devices for providing vibrations or other tactile feedback, speakers for providing audible instructions, beeps, or other audible tones; or any other methods for receiving commands, settings, or other input from a user and providing information or output to the user. User interfaces 28 may also include one or more displays 32, one or more of which may be touchscreens for receiving user input. One or more user interfaces 28 or portions thereof may be included in a separate housing from the treatment device, such as in a smart charging dock or a personal computer, and the treatment device may communicate with the separate housing via hardwire (such as a cable or jack), wireless methods (such as infrared signals, radio signals, or Bluetooth), or other suitable communication methods.

Battery unit 20 may include any one or more batteries or battery cells for supplying power to laser unit 14 and/or additional components of device 10 (e.g., control electronics 50 of laser control system 30). For example, battery unit 20 may comprise one or more rechargeable or non-rechargeable batteries and/or connections for recharging battery unit 20, e.g., from a wall outlet. In some embodiments, battery unit 20 include one or more rechargeable or non-rechargeable batteries, e.g., one or more Li containing cells or one or more A, AA, AAA, C, D, prismatic, or 9V rechargeable or non-rechargeable cells. In particular, embodiments, battery unit 20 comprises a $LiFePO_4$ type battery or an $LiMn_xO_y$ type battery.

At least some embodiments of device 10 provide eye safe radiation. For example, the emitted laser radiation from device 10 may be inherently eye safe, e.g., based on the divergence of laser radiation emitted from the application end 42 of device 10, the wavelength of the radiation, the treatment pulse width, and/or other parameters of the emitted radiation. For example, in some embodiments or settings, device 10 the emitted radiation from device 10 meets the Class 1M or better (such as Class 1) eye safety classification per the IEC 60825-1. In addition, device 10 may provide a further layer of eye safety by incorporating an eye safety control system including one or more skin contact sensors, cornea-recognition sensors, etc., and suitable control electronics 30 for activating laser unit 14 only when the application end of the device is in contact with skin.

Figure 3:
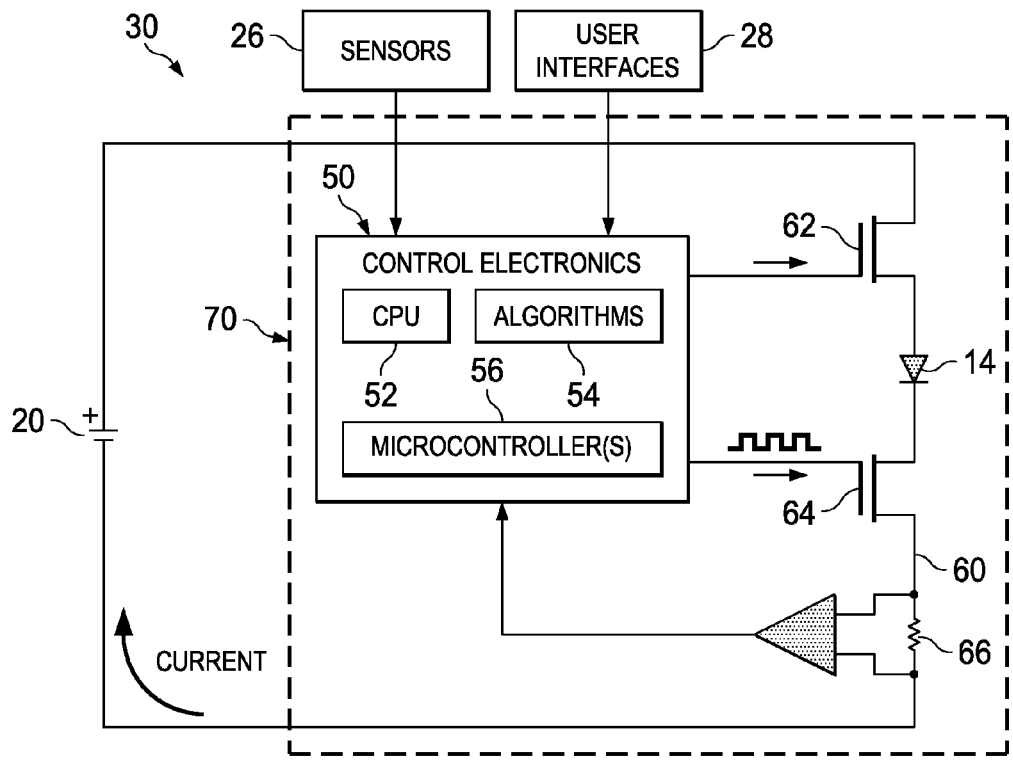
FIG. 3 illustrates an example laser control system for delivering current from a battery unit to a laser unit using PWM control, according to certain embodiments of the present invention.

FIG. 3 illustrates an example laser control system 30 for delivering current from a battery unit 20 to a laser unit 14 using PWM control, according to an example embodiment. As shown, laser control system 30 may include a laser drive circuit 60 and data inputs for laser drive circuit 60, including one or more sensors 26 and/or one or more user interfaces 28. Laser drive circuit 60 includes a laser unit 14 (in this example, a single laser diode), a battery unit 20, a first switch 62, a second switch 64, an optional current sense component 66, and control electronics 50 configured to receive data from one or more inputs (e.g., sensor(s) 26, user interface(s) 28, and/or current sense component 66) and control first switch 62 and second switch 64 based at least on such received input data. Such components may be arranged on a circuit board, indicated by dashed line 70. In some embodiments, laser drive circuit 60 is free of filtering electronics.

Laser unit 14 is configured to generate laser radiation for a dermatological treatment. Although includes a single laser diode in the illustrated example, laser unit 14 may include multiple laser diodes, one or more laser diode bars, or other laser structures, arranged in series or in parallel as appropriate. In some embodiments, the laser has a forward voltage drop of 1.85 V and can withstand 80 amps or more when pulsed with a duration of less than one second, e.g., for a hair removal treatment or a fractional treatment, for example.

As discussed above, battery unit 20 may include any one or more batteries or battery cells. In one embodiment, battery unit 20 comprises a single 18650-type $LiMn_xO_y$ battery with an open-circuit charged voltage of 4.2 V and an internal series resistance of 0.016 ohms, which is capable of generating 75 amps through the laser 14. The wires connecting the battery 20 to the circuit board 70 have some resistance, and some inductance due to the length of the wire.

First and second switches 62 and 64 may comprise transistors or any other type of switches. For example, first and second switches 62 and 64 may be field effect transistors (FETs). As discussed herein, the first switch 62 is configured as a safety switch, which is turned ON only when device 10 is properly configured and arranged to deliver radiation to the skin, e.g., when device 10 is turned on and properly held against the skin, and otherwise maintained in the OFF state. Thus, safety switch 62 acts as a safety device to prevent laser 14 from firing when device 10 is not properly configured and arranged to deliver radiation, e.g., in the event of a malfunction involving the control or operation of second switch 64 that would otherwise lead to the activation of laser 14. Safety switch 62 may be controlled (turned ON or OFF) by control electronics 50, e.g., a CPU 52 or microprocessor 56, based on data received from one or more inputs, e.g., sensor(s) 26 and/or user interface(s) 28.

Second switch 64, referred to herein as the "control switch," controls current to the laser 14 when safety switch 62 is switched to the ON state. In particular, control switch 64 is PWM-controlled by control electronics 50, e.g., a microcontroller 56, such that laser diode 14 receives a rapidly-switching PWM current waveform. In one embodiment, control switch 64 is a low-$R_{DS(on)}$ FET device. The instantaneous current through the laser diode 14 while control switch 64 is turned on is limited by parasitic resistance and inductance of the components and leads of circuit 60.

In an example embodiment, control switch 64 is a FET with an on resistance $R_{DS(on)}$ of less than 2 milli-ohms, such that with a current of, e.g., 50 amps, the voltage drop across FET 64 is less than 0.1 volts. FET 64 is turned on and off by a logic-level control signal, e.g., generated by a microcontroller 56.

As shown, first and second switches 62 and 64 may be arranged in series with laser 14, with laser 14 arranged between the first and second switches 62 and 64. This arrangement allows switches 62 and 64 to address a potential short on either side of laser 14.

Current sense component 66 may include an analog current-sense amp measures the current and sends the measurement signal to CPU 52, which may use such measurement for monitoring device status and battery state of charge. This current measurement is not necessary for the control system to operate, and is thus omitted in some embodiments. That is, the PWM control system 30 can operate "open-loop" on a short or long timescale.

Control electronics 50 may include any hardware, software, and/or firmware configured to control the operation of laser control system 30, including, e.g., controlling first and second switches 62 and 64. Control hardware may include one or more processors, microcontrollers, non-transitory memory devices, transistors, resistors, capacitors, inductors, transformers, diodes, amplifier circuits, and/or any other hardware devices. In the illustrated example, control electronics includes CPU 52, algorithms 54, and microcontroller 56. Algorithms 54 may be embodied as software or firmware, and may be stored in any suitable non-transitory memory device (e.g., flash memory, RAM, ROM, EEPROM, etc.) and executable by CPU 52. Microcontroller 56 may also include integrated memory that stores suitable algorithms. In one embodiment, CPU 52 may send control signals to microcontroller 56 to control switches 62 and 64. In other embodiments, switches 62 and 64 are directly controlled by separate devices, e.g., separate CPUs or microcontrollers, such that a fault in one device (e.g., one of two microcontrollers) does not affect both switches 62 and 64, thereby providing an additional safety aspect.

In operation, control electronics 50 control the operation of laser 14 by controlling safety FET 62 and control FET 64 as disclosed herein. In particular, control electronics 50 turns safety FET 62 "on" when device 10 is turned on (manually or automatically) and properly arranged for delivering radiation, e.g., as determined based on signals from sensor(s) 26 and/or user interface(s) 28. Control electronics 50 also apply control signals to control FET 64 to activate laser unit 14. For continuous wave (CW) radiation, control electronics 50 generate and apply a PWM signal to laser 14 for a predetermined duration or for a duration based on feedback from sensor(s) 26, e.g., as long as sensors 26 detect (a) sufficient skin contact according to predefined threshold(s) and/or (b) sufficient movement of the device according to predefined threshold(s). For pulsed radiation, the control signals applied to laser 14 define two levels of pulsing, including (a) a treatment pulse signal that defines individual "macro" treatment pulses, and (b) PWM control of each individual treatment pulse, which defines "micro" pulses. The control signals may define the relevant parameters of both the treatment pulse profile and the PWM profile, e.g., the frequency, duty cycle, pulse-on duration, and/or pulse-off duration for each level of pulsing.

To provide the PWM control (in both CW and pulsed radiation modes), control electronics 50, e.g., a microcontroller 56, applies a rapidly-switching PWM waveform, which forms a digital ON/OFF voltage, to the control FET 64. As a result of such waveform, control FET 64 is almost always either fully on (high current but low resistance=low power dissipation) or fully off (substantially no current and no power dissipation), with minimal time in the in-between linear region in which power dissipation increases, thus generating less heat on the circuit board 70 and better reliability, as compared to a linear control circuit. Further, the digital control system 30 generating PWM has fewer and less expensive parts than a conventional analog linear control system and is also more stable over time.

In an example embodiment, a high-current $LiMn_xO_yCo_z$ battery 20 can deliver 75 A peak and 50 A time-averaged power into a laser diode 14 with a forward voltage drop of 1.85V, using a 67% duty cycle pulse width modulation (PWM) driver (e.g., provided by a microcontroller 56). When the laser 14 is used in a dermatological treatment device that depends on tissue heating on a millimeter size scale or larger, a PWM current drive at a high enough frequency (for example, 20 kHz or above) will have the same effect as a DC current drive with the same average current.

Use of a PWM current drive by control system 30 enables lower power dissipation on the printed circuit board 70 in several ways over a linear control circuit. First, with the PWM control, the power dissipation of the linear control element is absent from the PCB. In addition, the inductance of the battery leads limits the current risetime as the control switch 64 is turned on, so current can be limited by varying the switch on-time duration without relying on a resistive element that incurs $I^2R$ heating losses. The inductance can be chosen to the suit the application. For example, in some embodiments, the shortest practical lead length to connect an 18650 size (18 mm diameter×65 mm long) battery to a PCB is about 75 mm. The inductance of a 16-gauge (1.291 mm diameter) copper wire 75 mm long (neglecting high-frequency skin effects) is about 70 nH (nano-Henries). In other embodiments, as discussed below with reference to FIG. 6, the inductance can be reduced by using the conductive outer case of the battery as the cathode connection, thereby eliminating a length of lead extending along the length of the battery 20.

Assuming a configuration with a lead inductance of 70 nH. The voltage across a circuit element with nonzero inductance and resistance is given by V=I*R+L(dI/dt). If we switch 75 A in 2 microseconds, (dI/dt)=75/(2E-6)=3.75E7 V/sec. Thus, the relatively small inductance of 70 nH creates a voltage across the inductor of V=(3.75E7 V/sec)*(7E-8 H)=2.62 volts. In other words, with an available drive voltage of 2.62 V we would cause a current ramp that reaches 75 A after 2 microseconds. Should a lower peak current be desired, the drive voltage could be turned off before that point. There is relatively little voltage overhead from resistance in this circuit. For example, a 75 mm length of 16-gauge copper wire has a resistance of 0.96 mOhm so the voltage drop due to resistance of this wire at 75 A is V=IR=(75 A)*(9.6E-4 ohms)=72 mV.

Using a PWM control circuit 60 results in higher instantaneous current through the battery and the battery leads than a linear control circuit with the same DC-average current. Because power dissipation through a resistance is proportional to the square of the current ($P=I^2R$), while the average power output of the laser device is essentially proportional to current and is a simple time average (linear with duty cycle), using PWM control therefore causes more heating of the battery 20 and adjacent leads than linear control, for the same time-averaged power output. This additional heating is advantageous for batteries that can deliver more energy at higher internal temperature, such as $LiFePO_4$ and $LiMn_xO_yCo_z$ type batteries, for example. Such batteries typically provide a maximum power output when operating at an internal temperature of about 40-70° C. The PWM circuit 60 also deposits relatively less heat energy on the PCB 70, where it is not wanted because the $R_{DS(on)}$ resistance of the control FET 64 increases with temperature, and temperature rise can adversely affect performance of other circuits located there.

Further, because the laser diode 14 typically has a non-zero dark current, higher currents give higher total optical output efficiencies, up until the point where a drop in optical efficiency due to temperature rise overcomes this benefit.

Figure 4:
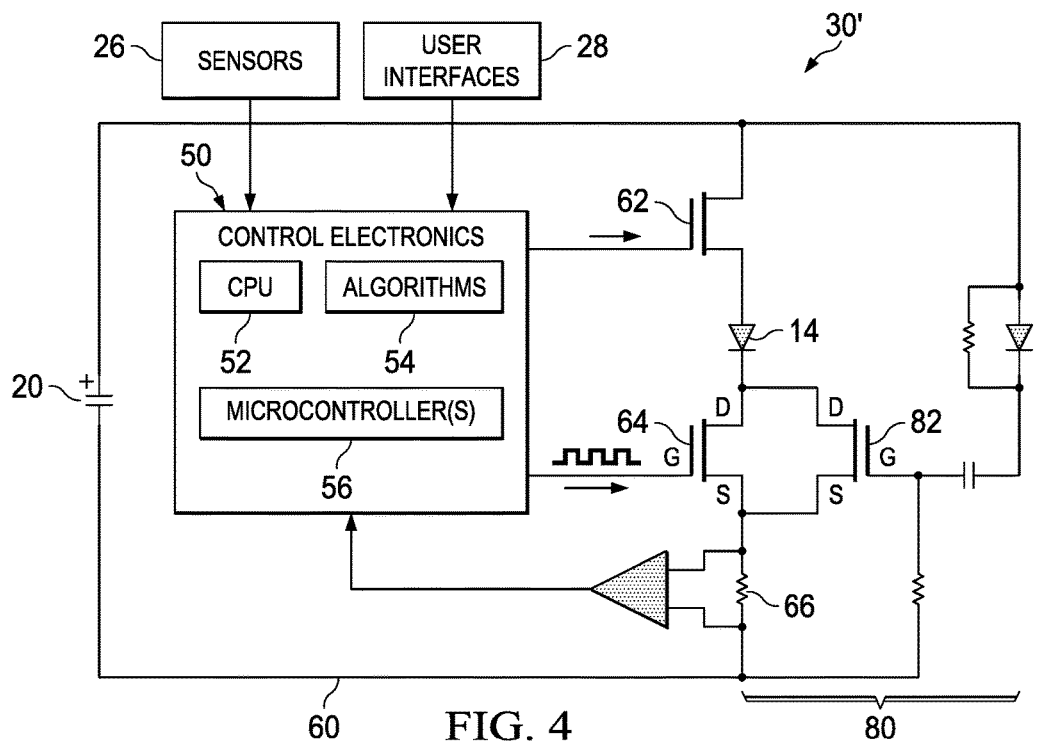
FIG. 4 illustrates an example laser control system similar to the embodiment of FIG. 3, but further including a snubber circuit for preventing voltage overshoot, according to certain embodiments of the present invention.

FIG. 4 illustrates an example laser control system 30' similar to the embodiment of FIG. 3, but further including a snubber circuit 80 for preventing voltage overshoot, according to certain embodiments. As shown, snubber circuit 80 may include a snubber switch 82 (e.g., a FET) and other suitable circuit components, and configured to prevent the occurrence of voltage spikes upon the second switch 64 being turned off. The snubber switch 82 is connected in parallel with the control switch 64 with the respective source (S), drain (D), and gate (G) terminals arranged as shown.

Any voltage spike on the V+ supply caused by fast switching action of the control switch 64, drives the gate of the snubber switch 82 on and allows current to flow in reaction, so that the voltage spike is reduced before getting very large. Alternatively, a similar effect can be achieved without a snubber switch 82 by slowing down the falling edge of the PWM drive into control switch 64.

Figure 5:
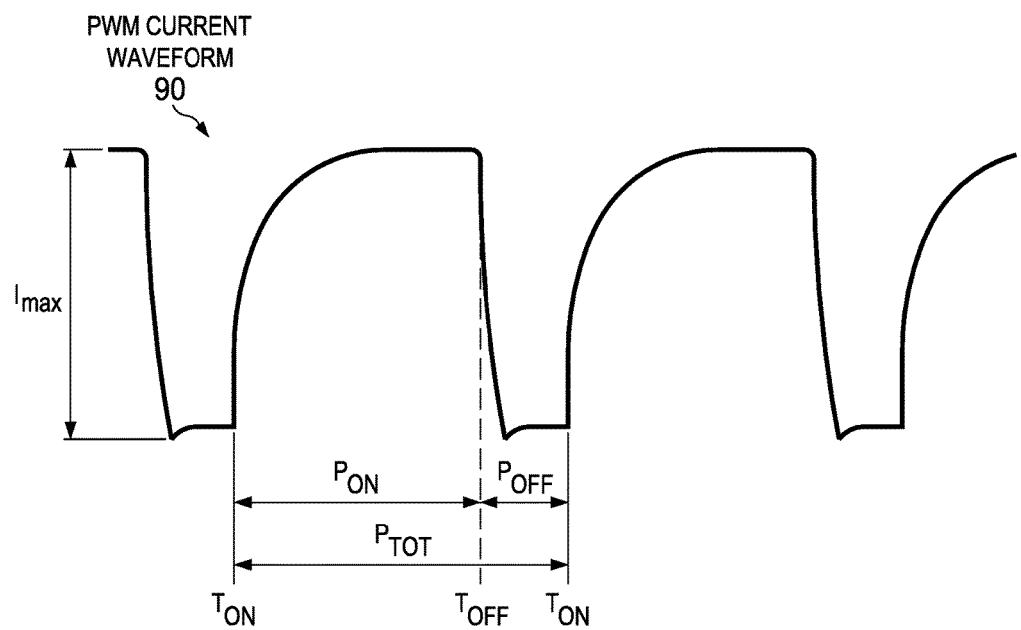
FIG. 5 illustrates an example PWM current waveform delivered to a laser using a PWM laser control system, according to certain embodiments of the present invention.

FIG. 5 illustrates an example PWM current waveform 90 delivered to a laser using the PWM laser control system 30 or 30' of FIG. 3 or 4, according to an example embodiment. PWM current waveform 90 applied to laser 14 may be generated by controlling switch 64 using a PWM signal generated by control electronics 50, e.g., a microcontroller 56. In particular, control switch 64 is switched on at $T_{ON}$ and switched off at $T_{OFF}$. The time between $T_{ON}$ and $T_{OFF}$ is referred to as the pulse-on duration, indicated as $P_{ON}$, while the time between $T_{OFF}$ and $T_{OFF}$ is referred to as the pulse-off duration, indicated as $P_{OFF}$. The sum of each pulse-on duration $P_{ON}$ and subsequent pulse-off duration, $P_{OFF}$, is referred to as the total pulse duration, indicated as $P_{TOT}$. The duty cycle for the PWM current waveform is calculated as $P_{ON}/(P_{ON}+P_{OFF})$, or $P_{ON}/P_{TOT}$, while the frequency is the inverse of the total pulse duration (frequency=$1/P_{TOT}$). The maximum, or peak, current of each pulse is indicated by $I_{MAX}$.

Control electronics 50 may set and dynamically control the frequency and duty cycle of waveform 90, based on various input, e.g., a user-selected device setting (e.g., operational mode, or low/medium/high power setting, etc.) and/or data from one or more sensors 26. In some embodiments, the frequency of PWM current waveform 90 may be in the range of 10-100 Hz, e.g., 20-25 Hz, while the duty cycle may be in the range of 30-60%.

In some embodiments, PWM current waveform 90 may be adjusted in real time. For example, in pulsed radiation applications, e.g., for providing a hair removal or fractional treatment, PWM current waveform 90 may be adjusted in real time during each individual pulse. Specifically, the frequency and/or duty cycle may be adjusted one or more times during each individual pulse.

The disclosed PWM control system provides various advantages over a conventional linear constant-current drive system that provides a similar time-averaged power output. For example, using PWM control enables the use of fewer components in the control system, lowering the overall cost of the system. It also reduces the heat generated on the PCB, where it is typically unwanted and expensive to remove, and generates additional I²R heating at the battery, where may increase the battery performance as increased internal battery temperature increases the total available energy from the battery, at least for certain types of batteries. In other words, the PWM control system shifts energy dissipation, and thus heat generation, from the PCB to the battery itself, which may be advantageous. Further, the disclosed PWM control system provides digital control of laser energy by controlling the duty cycle (thereby controlling the pulse-on time), instead of analog control of the voltage level.

Example Test Results

A prototype of a device having a PWM control system as disclosed in FIG. 3 was constructed and tested. The battery output as a function of battery temperature was measured, starting with a fully charged battery with resting voltage of 4.2 V and using the cutoff criterion of 42A average over a fixed-length 650 msec PWM pulse into a 0.025 ohm load. The testing showed the following battery output:

1822 mAh and 2223 mWh at battery temperature=33 C
1898 mAh and 2359 mWh at battery temperature=50 C Wherein:
Battery temperature=averaged temperature during discharge, measured by a thermocouple at the center of the cell, enclosed in stirred water bath to maintain temperature;
mAh=milliamp-hours, calculated using the instantaneous current measured at the load, integrated over the full discharge from the fully charged state; and
mWh=milliwatt-hours, calculated using the instantaneous power measured at the load (P=V*I) integrated over the full discharge.

Thus, the 17° C. temperature increase of the battery provides a 6% improvement in the energy (2359 mWh vs. 2223 mWh) delivered to the load, i.e., the laser.

As mentioned above, the inductance of the PWM laser drive circuit can be reduced by using the conductive outer case of the battery 20 as the cathode connection, thereby eliminating a length of lead extending along the length of the battery 20.

Figure 6A:
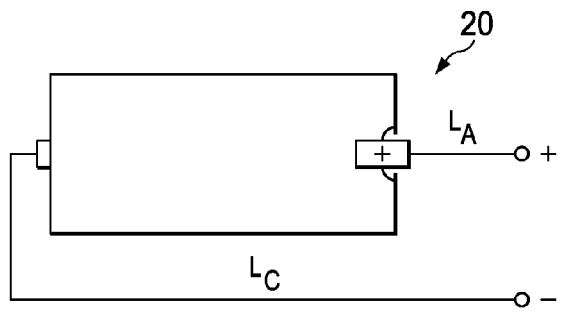
FIG. 6A illustrates a conventional arrangement of a battery with the anode and cathode leads connected at opposite ends of the battery.
Figure 6B:
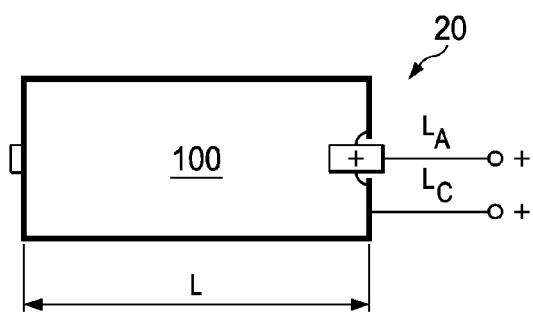
FIG. 6B illustrates a battery with a conductive outer shell that acts as an electrical lead such that the anode and cathode leads can be connected at the same end of the battery, according to an example embodiment of the present invention.

FIGS. 6A and 6B illustrate an example of this technique for reducing the drive circuit inductance. FIG. 6A illustrates a conventional arrangement of a battery 20 with the anode and cathode leads $L_A$ and $L_C$ connected at opposite ends of the battery. In contrast, FIG. 6B illustrates a battery 20 with a conductive outer shell 100 that acts as an electrical lead such that the anode and cathode leads $L_A$ and $L_C$ can be connected at the same end of the battery 20. Thus, the length of the cathode lead $L_C$ can be reduced by at least the length of the battery, indicated in FIG. 6B as length L.

Although the disclosed embodiments are described in detail in the present disclosure, it should be understood that various changes, substitutions and alterations can be made to the embodiments without departing from their spirit and scope.

The invention claimed is:

1. A dermatological treatment device, comprising:
a laser unit comprising at least one laser diode configured to emit laser radiation at a wavelength between 1400 nm and 2000 nm, suitable for non-ablative fractional photothermolysis;
a battery unit;
at least one sensor configured to generate sensor signals;
an application end configured to be manually moved across a surface of a user's skin during delivery of laser radiation emitted by the laser unit;
a laser control system, comprising:
a laser drive circuit comprising the laser unit, the battery unit, a first switch, and a second switch;
wherein the laser unit is arranged in series between the first switch and the second switch;
control electronics comprising computer instructions stored in non-transitory computer-readable media and executable by a processor to control the laser unit during manual movement of the application end across the surface of the user's skin, to provide a fractional photothermolysis treatment in the skin by generating a sequential series of discrete, non-continuous wave (non-CW) treatment pulses at the wavelength between 1400 nm and 2000 nm delivered to the skin to form a sequential series of non-ablative treatment spots spaced apart from each other on the skin by:
controlling the first switch based at least on sensor signals from the at least one sensor;
controlling the second switch using multi-level pulsing control signals including:
(a) treatment pulse control signals defining at least one pulse characteristic for each of the sequential series of discrete, non-CW treatment pulses, each treatment pulse having a treatment pulse duration in a range between 0.5 ms and 10 ms and producing a corresponding non-ablative treatment spot on the skin, and
(b) pulse width modulation (PWM) control signals that define a PWM waveform within each of the discrete, non-CW treatment pulses, thereby delivering current from the battery unit to the laser unit with a PWM current waveform during each treatment pulse,
wherein the PWM current waveform for each treatment pulse includes a series of multiple PWM pulses that forms a single treatment spot in the skin that is spaced apart from other treatment spots formed by other treatment pulses by non-treated areas of skin, to thereby provide the fractional photothermolysis treatment in the skin.

2. The dermatological treatment device according to claim 1, wherein the first switch is a first field effect transistor (FET) and the second switch is a second FET.

3. The dermatological treatment device according to claim 1, wherein the laser drive circuit is free from filtering electronics.

4. The dermatological treatment device according to claim 1, wherein the control electronics are configured to control the second switch using PWM such that a temperature of the battery unit is increased and maintained within a temperature range of 40-70° C.

5. The dermatological treatment device according to claim 1, wherein the laser drive circuit further comprises a snubber circuit configured to prevent the occurrence of voltage spikes upon the second switch being turned off.

6. The dermatological treatment device according to claim 1, wherein the control electronics are configured to automatically control at least one of a frequency or a duty cycle of the PWM current waveform based on a user selected setting.

7. The dermatological treatment device according to claim 1, wherein the control electronics are configured to dynamically adjust at least one of a frequency or a duty cycle of the PWM current waveform for a particular treatment pulse in real time during the particular treatment pulse.

8. A control system for a dermatological treatment device including a laser unit comprising at least one laser diode configured to emit laser radiation at a wavelength between 1400 nm and 2000 nm, suitable for non-ablative fractional photothermolysis, a battery unit, and at least one sensor configured to generate sensor signals, the control system comprising:
 a laser drive circuit comprising the laser unit, the battery unit, a first switch, and a second switch;
 wherein the laser unit is arranged in series between the first switch and the second switch;
 control electronics configured to control the laser unit, during manual movement of the dermatological treatment device across the surface of the user's skin, to generate a sequential series of discrete, non-continuous wave (non-CW) treatment pulses at the wavelength between 1400 nm and 2000 nm and delivered to a user's skin to form a sequential series of non-ablative treatment spots spaced apart from each other on the skin by:
 controlling the first switch based at least on sensor signals from the at least one sensor;
 controlling the second switch using multi-level pulsing control signals including:
  (a) treatment pulse control signals defining at least one pulse characteristic for each of the sequential series of discrete, non-CW treatment pulses at the wavelength between 1400 nm and 2000 nm suitable for non-ablative fractional photothermolysis, each treatment pulse having a treatment pulse duration in a range between 0.5 ms and 10 ms and producing a corresponding non-ablative treatment spot on the skin, and
  (b) pulse width modulation (PWM) control signals that define a PWM waveform within each of the discrete, non-CW treatment pulses, thereby delivering current from the battery unit to the laser unit with a PWM current waveform during each treatment pulse,
 wherein the PWM current waveform for each treatment pulse includes a series of multiple PWM pulses that forms a single treatment spot in the skin that is spaced apart from other treatment spots formed by other treatment pulses by non-treated areas of skin, to thereby provide a fractional photothermolysis treatment in the skin.

9. The control system according to claim 8, wherein the first switch is a first field effect transistor (FET) and the second switch is a second FET.

10. The control system according to claim 8, wherein the laser drive circuit is free from filtering electronics.

11. The control system according to claim 8, wherein the control electronics are configured to control the second switch using PWM such that a temperature of the battery unit is increased and maintained within a temperature range of 40-70° C.

12. The control system according to claim 8, wherein the laser drive circuit further comprises a snubber circuit configured to prevent the occurrence of voltage spikes upon the second switch being turned off.

13. The control system according to claim 8, wherein the control electronics are configured to automatically control at least one of a frequency or a duty cycle of the PWM current waveform based on a user selected setting.

14. The control system according to claim 8, wherein the control electronics are configured to dynamically adjust at least one of a frequency or a duty cycle of the PWM current waveform for a particular treatment pulse in real time during the particular treatment pulse.

15. A control system for a dermatological treatment device including a laser unit comprising at least one laser diode, a battery unit, and at least one sensor configured to generate sensor signals, the control system comprising:
 a laser drive circuit comprising the laser unit, the battery unit, a first switch, and a second switch;
 wherein the laser unit is arranged in series between the first switch and the second switch; and
 control electronics configured to:
  control the first switch based at least on sensor signals from the at least one sensor; and
  control the second switch using pulse width modulation (PWM) during each of a series of discrete, non-continuous wave (non-CW) treatment pulses, each treatment pulse having a treatment pulse duration in a range between 1 ms and 700 ms, thereby delivering current from the battery unit to the laser unit with a PWM current waveform during each treatment pulse, wherein the PWM current waveform for each treatment pulse includes a series of multiple PWM pulses within the respective treatment pulse;
  receive sensor signals generated by the at least one sensor based on an interaction with a user's skin; and dynamically adjust at least one waveform profile parameter of the PWM current waveform for a particular treatment pulse in real time during the particular treatment pulse based on the received sensor signals.

16. The control system according to claim 15, wherein dynamically adjusting at least one waveform profile parameter of the PWM current waveform for a particular treatment pulse in real time during the particular treatment pulse comprises dynamically adjusting at least one of a frequency or a duty cycle of the PWM current waveform for the particular treatment pulse in real time during the particular treatment pulse.

* * * * *